United States Patent [19]
Dolan et al.

[11] Patent Number: 5,975,296
[45] Date of Patent: Nov. 2, 1999

[54] DENTAL FLOSS HOLDER

[75] Inventors: John W. Dolan, Boothwyn, Pa.; Brad F. Abrams, Cherry Hill, N.J.; Robert M. Russell, Newark, Del.; Harold J. Pickar, Sr., Pottstown; David D. McClanahan, Harleysville, both of Pa.

[73] Assignee: Gore Enterprise Holdings, Inc., Newark, Del.

[21] Appl. No.: 08/958,784

[22] Filed: Oct. 27, 1997

[51] Int. Cl.⁶ .................................................. A61C 15/00
[52] U.S. Cl. .......................................... 206/368; 132/323
[58] Field of Search ................................. 206/368, 63.5; 132/309, 323–327

[56] References Cited

U.S. PATENT DOCUMENTS

| | | | |
|---|---|---|---|
| D. 237,499 | 11/1975 | Maloney et al. | D24/99 |
| D. 251,075 | 2/1979 | Schiff | 132/323 |
| D. 285,369 | 8/1986 | Morin et al. | D28/64 |
| D. 309,041 | 7/1990 | Schneider | D28/64 |
| D. 310,582 | 9/1990 | Kujirai | D28/64 |
| D. 348,332 | 6/1994 | Haggett-King et al. | D28/64 |
| D. 356,394 | 3/1995 | Daugherty | D28/64 |
| D. 374,311 | 10/1996 | Dolan et al. | D28/64 |
| D. 374,744 | 10/1996 | Dolan et al. | D28/64 |
| 788,947 | 5/1905 | Roth . | |
| 1,110,680 | 9/1914 | Gamble | 132/325 |
| 1,618,351 | 2/1927 | Raycraft . | |
| 1,627,525 | 5/1927 | Munro | 132/324 |
| 1,916,653 | 7/1933 | Bodde | 132/326 |
| 2,354,454 | 7/1944 | Geffner | 132/91 |
| 2,384,712 | 9/1945 | Turenchalk et al. | 132/327 |
| 2,735,436 | 3/1956 | Russo | 132/91 |
| 3,533,420 | 10/1970 | Maloney et al. | 132/92 |
| 3,592,203 | 7/1971 | Johnson | 132/91 |
| 3,834,404 | 9/1974 | Chien | 132/91 |
| 3,882,879 | 5/1975 | Lucas | 132/92 |
| 3,913,927 | 10/1975 | Day | 132/92 |
| 3,915,178 | 10/1975 | Zellers | 132/92 |
| 3,949,769 | 4/1976 | Minka | 132/91 |
| 3,960,159 | 6/1976 | Tesberg | 132/90 |
| 4,005,721 | 2/1977 | Yasumoto | 132/91 |
| 4,008,728 | 2/1977 | Sanchez | 132/92 |
| 4,014,354 | 3/1977 | Garrett | 132/91 |
| 4,016,892 | 4/1977 | Chodorow | 132/91 |
| 4,022,229 | 5/1977 | Minka | 132/92 |
| 4,031,909 | 6/1977 | Kelley | 132/91 |
| 4,041,962 | 8/1977 | Johannsson et al. | 132/91 |
| 4,052,994 | 10/1977 | Thun | 132/92 |
| 4,162,687 | 7/1979 | Lorch | 132/91 |
| 4,192,230 | 3/1980 | Johnson | 132/323 |
| 4,206,774 | 6/1980 | Griparis | 132/92 |
| 4,522,216 | 6/1985 | Bunker | 132/92 |
| 4,556,074 | 12/1985 | Morin et al. | 206/53 |
| 4,615,349 | 10/1986 | Kukuruzinski | 132/91 |
| 4,655,233 | 4/1987 | Laughlin | 132/91 |
| 4,655,234 | 4/1987 | Bowden | 132/92 |

(List continued on next page.)

FOREIGN PATENT DOCUMENTS 0 611 533   8/1994   European Pat. Off. .

*Primary Examiner*—Jim Foster
*Attorney, Agent, or Firm*—Allan M. Wheatcraft

[57] ABSTRACT

A dental floss holder includes a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a first position in which the first end portions of the arms diverge away from one another, and a second position in which the first end portions are moved toward one another. Dental floss material has one end secured to the first end portion of one arm and an opposite end secured to the first end portion of the other arm. The dental floss material has a first tension when the first end portions are in their spaced apart position and a second tension when the first end portions are moved toward one another, said first tension being greater than the second tension. Further embodiments of the dental floss holder are also contemplated.

23 Claims, 8 Drawing Sheets

U.S. PATENT DOCUMENTS

| | | | |
|---|---|---|---|
| 4,671,307 | 6/1987 | Curbow et al. | 132/91 |
| 4,729,392 | 3/1988 | Tenny | 132/91 |
| 4,736,757 | 4/1988 | Badoux | 132/91 |
| 4,738,271 | 4/1988 | Bianco | 132/92 |
| 4,790,336 | 12/1988 | Kuo | 132/325 |
| 4,807,752 | 2/1989 | Chodorow | 206/63.5 |
| 4,830,032 | 5/1989 | Jousson | 132/323 |
| 4,832,032 | 5/1989 | Grollimund et al. | 132/327 |
| 4,883,080 | 11/1989 | Lang | 132/332 |
| 4,936,326 | 6/1990 | Eckroat | 132/326 |
| 4,966,176 | 10/1990 | Lachenberg | 132/325 |
| 5,060,681 | 10/1991 | Westbrook et al. | 132/325 |
| 5,123,432 | 6/1992 | Wyss | 132/323 |
| 5,127,415 | 7/1992 | Preciutti | 132/323 |
| 5,176,157 | 1/1993 | Mazza | 132/322 |
| 5,188,133 | 2/1993 | Romanus | 132/325 |
| 5,197,498 | 3/1993 | Stewart | 132/325 |
| 5,253,662 | 10/1993 | Won | 132/325 |
| 5,279,314 | 1/1994 | Poulos et al. | 132/322 |
| 5,280,797 | 1/1994 | Fry | 132/323 |
| 5,287,865 | 2/1994 | Fulton | 132/323 |
| 5,323,796 | 6/1994 | Urso | 132/322 |
| 5,375,615 | 12/1994 | Wahlstrom | 132/325 |
| 5,400,811 | 3/1995 | Meibauer | 132/322 |
| 5,411,041 | 5/1995 | Ritter | 132/322 |
| 5,433,227 | 7/1995 | Chen | 132/323 |
| 5,538,023 | 7/1996 | Oszkowski et al. | 132/323 |
| 5,573,021 | 11/1996 | Grofcisk et al. | 132/324 |
| 5,657,780 | 8/1997 | Giacopuzzi | 132/325 |
| 5,664,592 | 9/1997 | Regnier | 132/323 |
| 5,692,531 | 12/1997 | Chodorow | 132/323 |
| 5,819,769 | 10/1998 | Gutierrez | 132/324 |

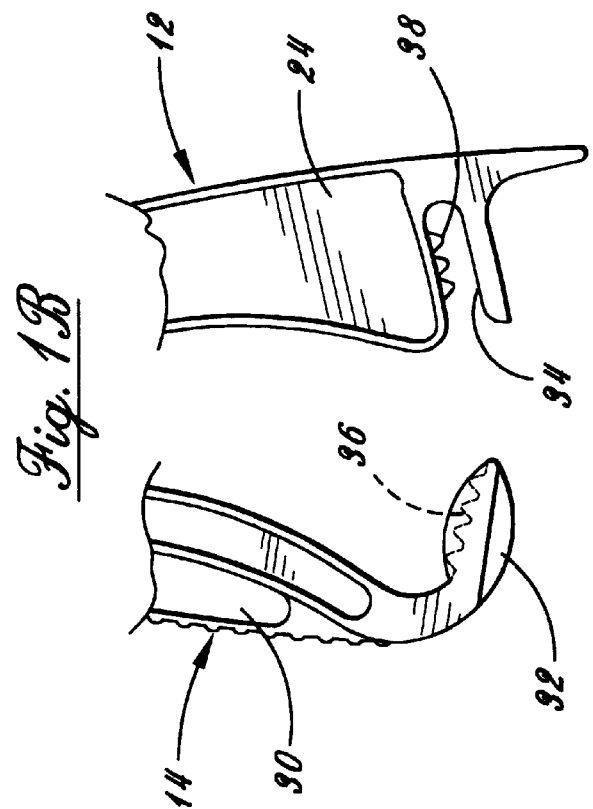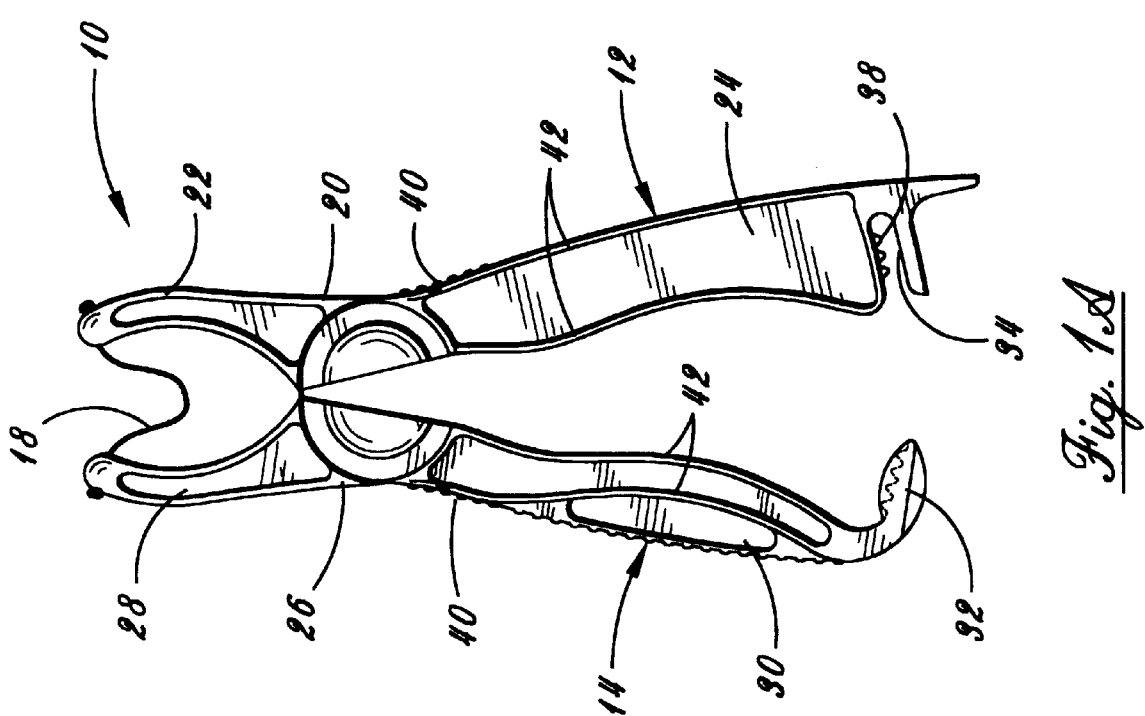

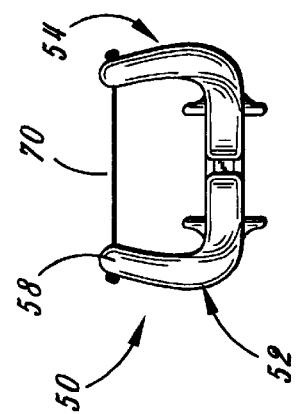
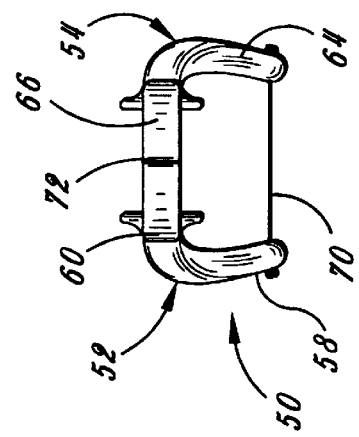
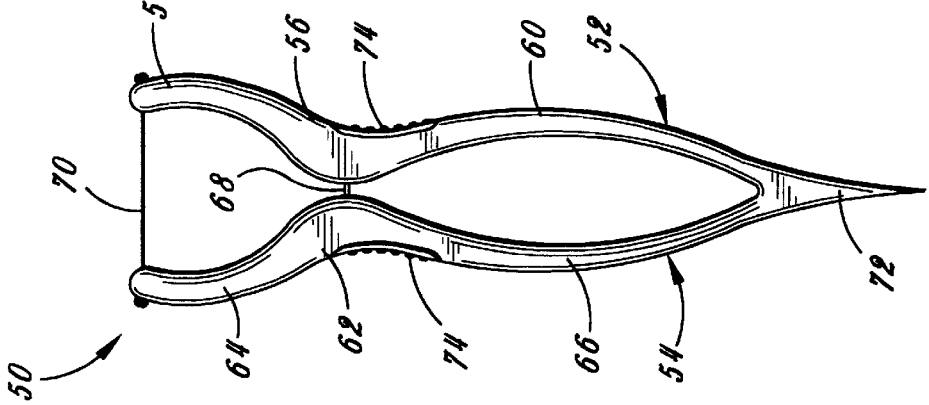
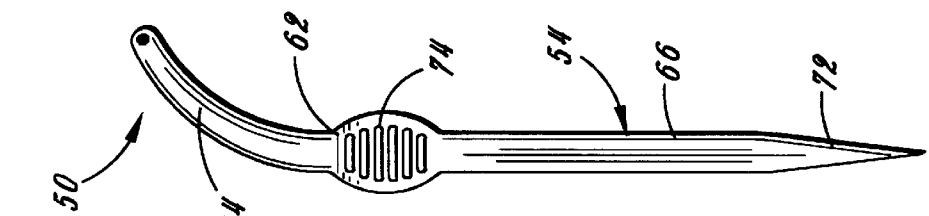
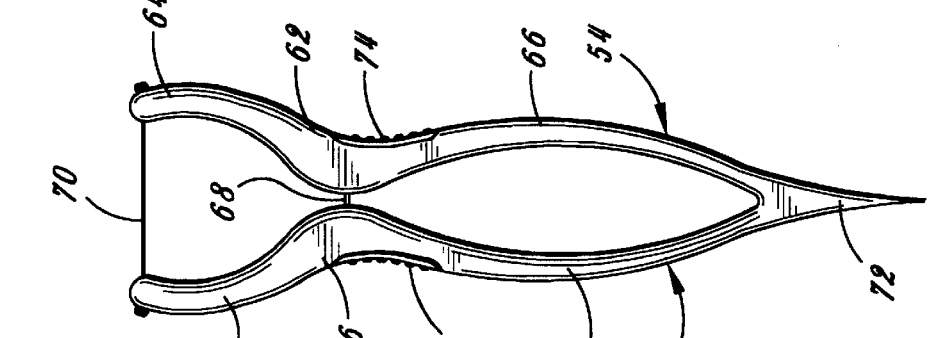
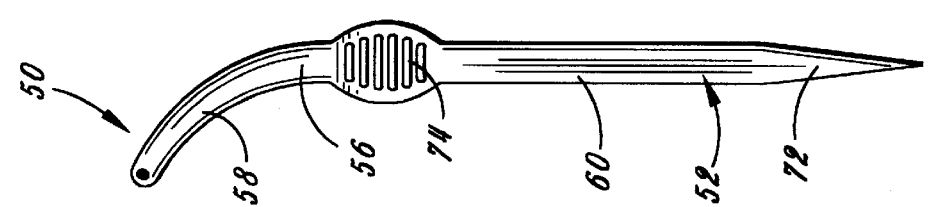

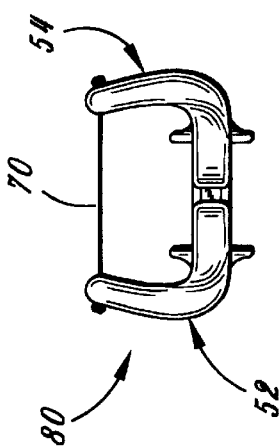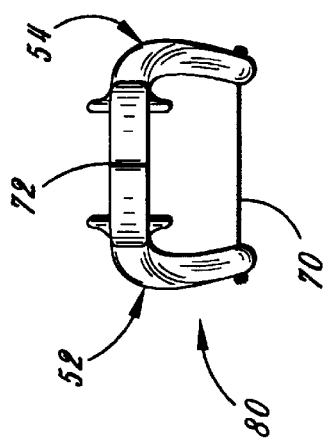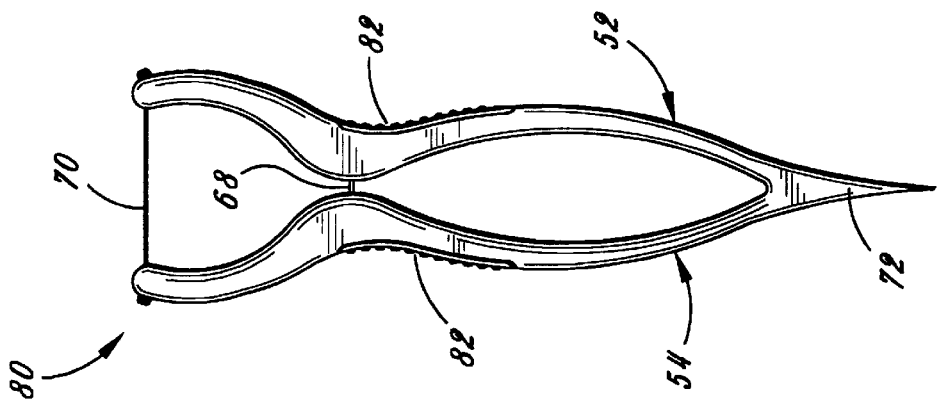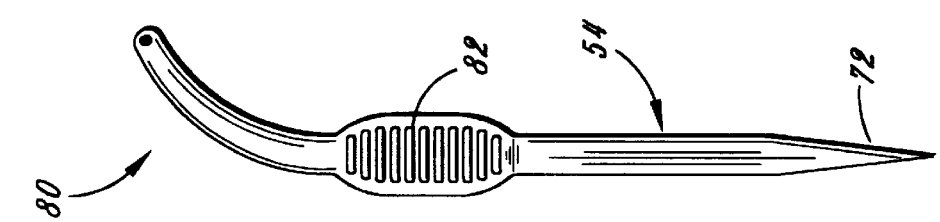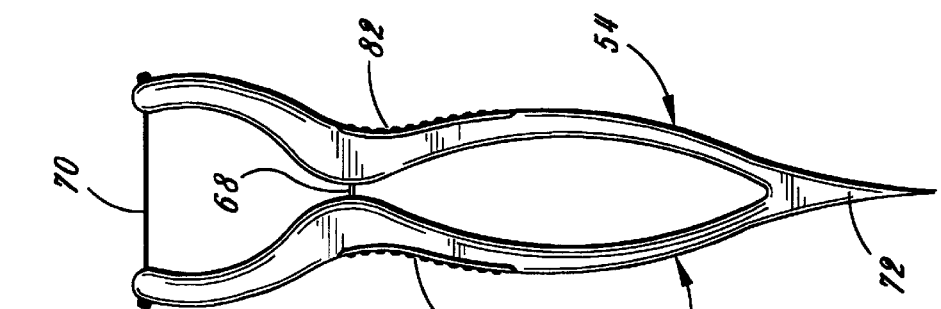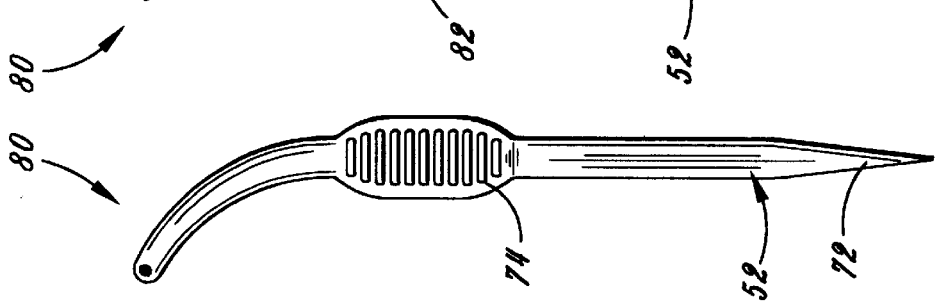

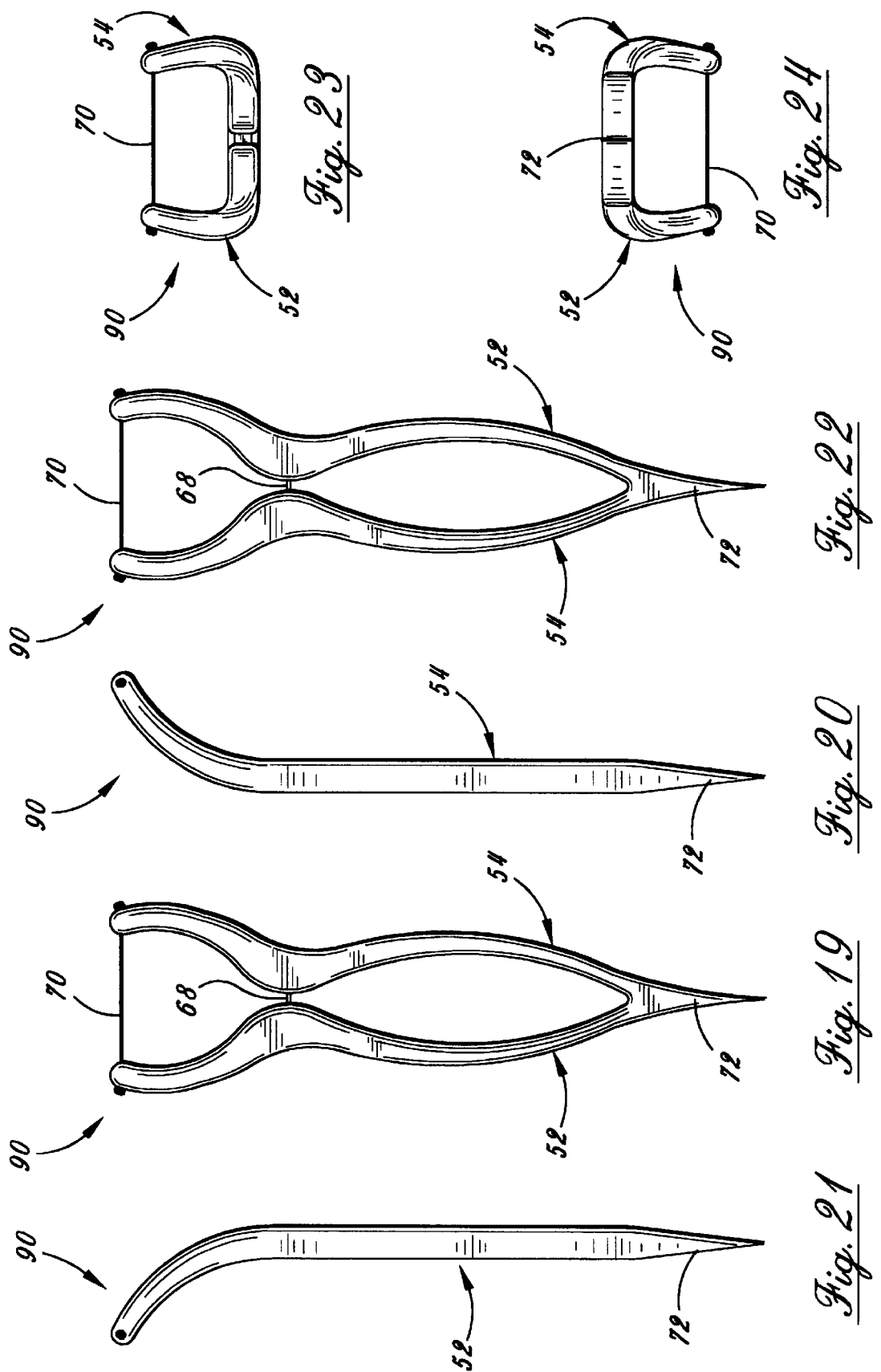

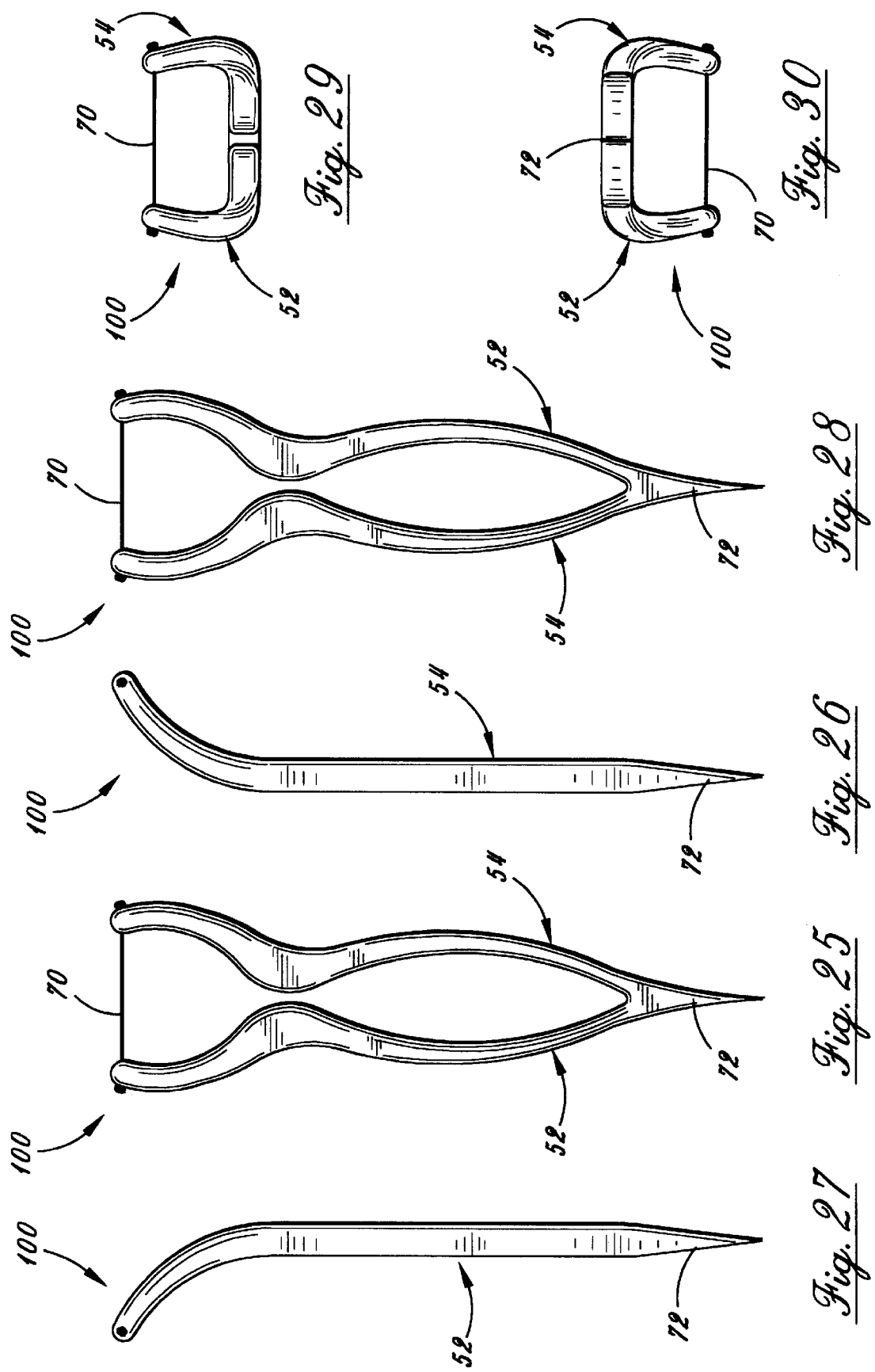

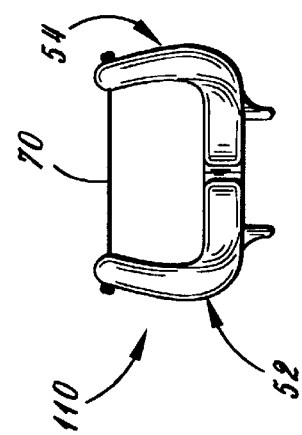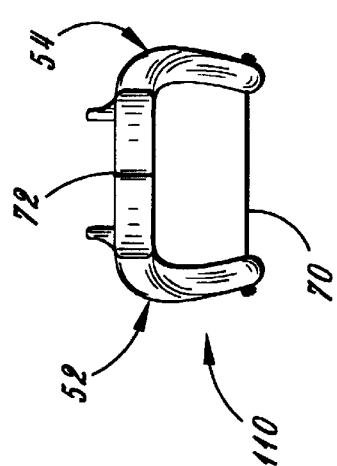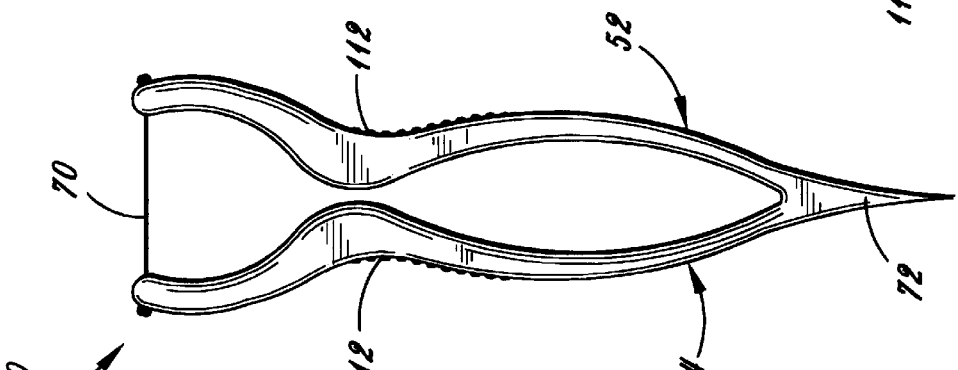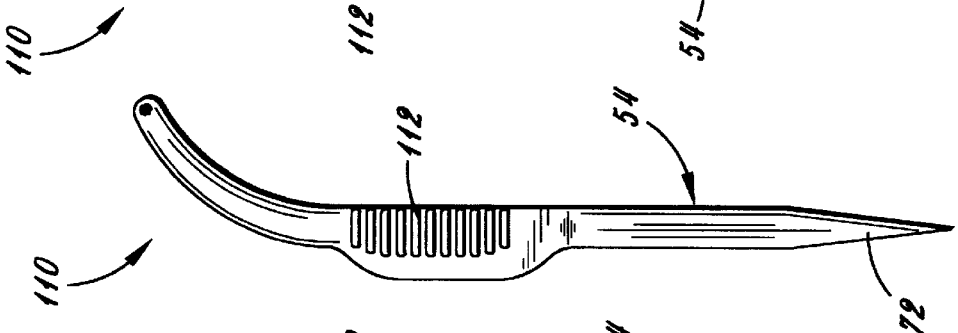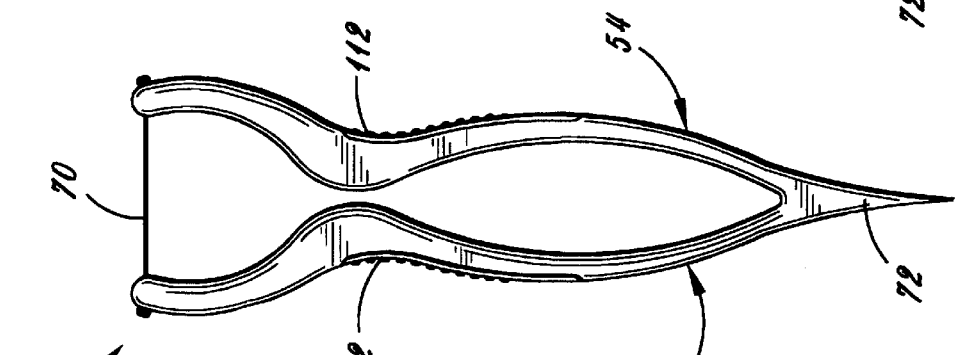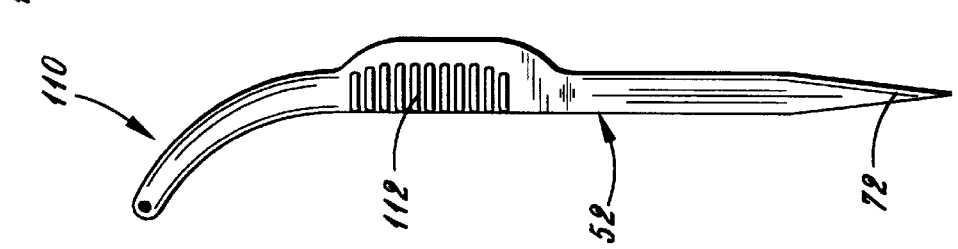

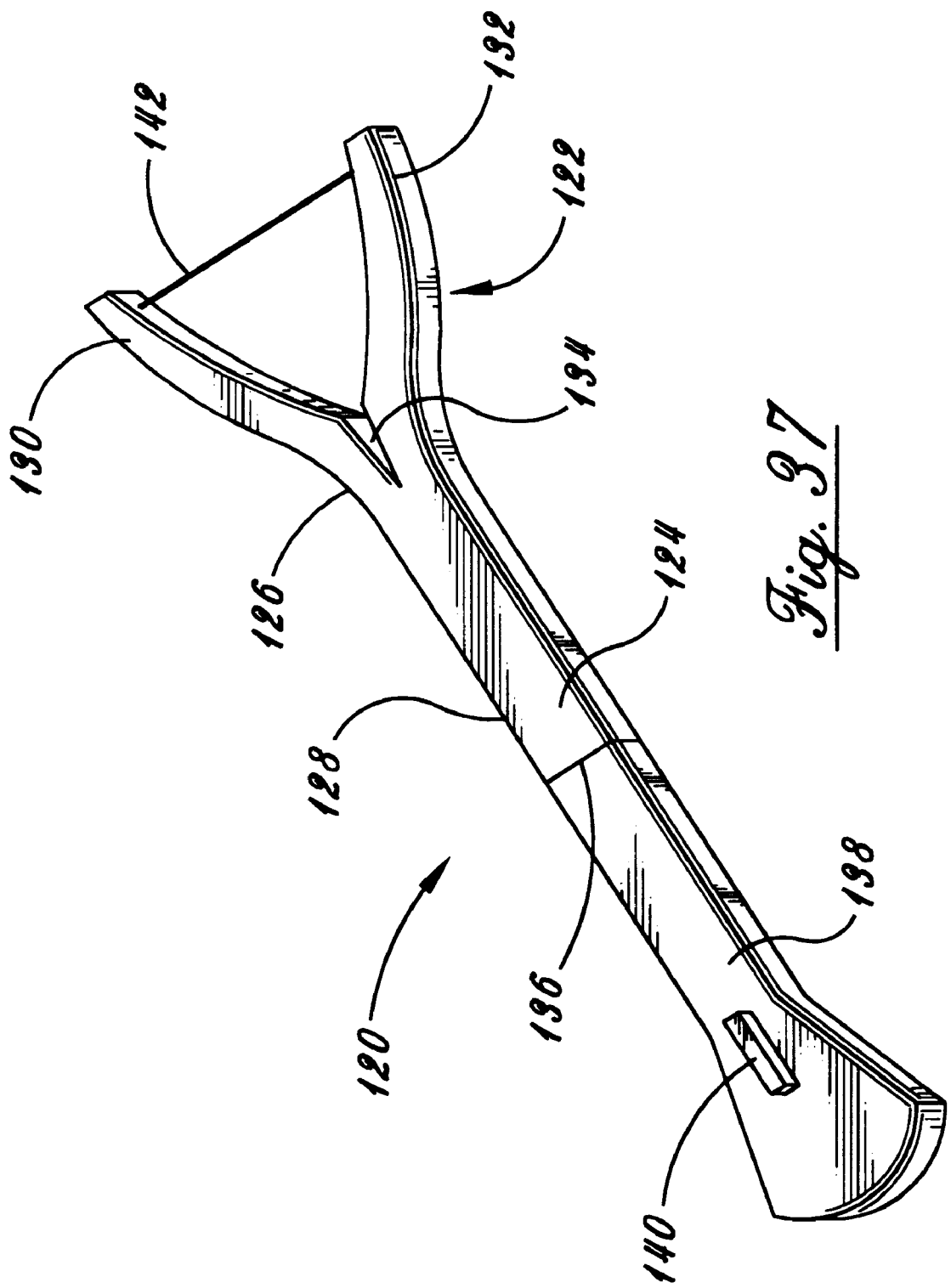

DENTAL FLOSS HOLDER

FIELD OF THE INVENTION

This invention generally relates to dental floss holders. More particularly, the present invention relates to a novel single use dental floss holder which is capable of, among other things, adjusting the tension of dental floss held by the holder.

BACKGROUND OF THE INVENTION

Dental floss holders are well known in the art. Such a prior art holder typically comprises a body having a linear portion for grasping the holder and a generally U-shaped or V-shaped end portion defined by a pair of fingers or tines which hold a string of dental floss material therebetween. The dental floss is securely fixed to the tines at opposite ends thereof by any well known manner. This construction of the dental floss holder enables the user to hold the linear portion while manipulating the dental floss between the user's teeth.

While the dental floss holder described above is suitable for its intended use, it does suffer from several disadvantages. For instance, prior to using the dental floss holder, the dental floss is fixed so that it can be manipulated between teeth. However, after forcing the dental floss many times between adjacent teeth, the dental floss stretches and becomes slack, thereby losing some of its initial tension. This makes it more difficult to manipulate the dental floss between teeth.

Additionally, during flossing of teeth, it is preferred to maintain the dental floss taut when initially inserting the floss between teeth, and, upon entering the space between the teeth, lessening the tension so that the dental floss wraps around the tooth being flossed. With the prior art dental floss holder described above, this preferred method of flossing one's teeth is impossible since the dental floss maintains only one tension, albeit this tension lessens as the dental floss holder is manipulated between one's teeth.

The foregoing illustrates some limitations known to exist in present dental floss holders. Thus, it is apparent that it would be advantageous to provide an improved dental floss holder directed to overcoming one or more of the limitations set forth above. Accordingly, a suitable alternative is provided including features more fully disclosed hereinafter.

SUMMARY OF THE INVENTION

The present invention advances the art of dental floss holders, and the techniques for creating such dental floss holders, beyond which is known to date.

In one embodiment of the present invention, a dental floss holder comprises a pair of arms or tines, each arm having a middle portion and first and second opposite end portions. The first end portion of each arm curves outwardly away from its respective middle portion wherein the middle portions of the arms are positioned proximate one another so as to define a pivot. The curvature permits the user to easily manipulate the dental floss device deep in the oral cavity without requiring the user to open his or her mouth extremely wide. Additionally, the area encompassing the yoke section, which is defined as the tines and the dental floss, is sufficiently large to permit the user to easily pass the dental floss around the molars. The second end portions are movable between a spaced apart position in which the second end portions of the arms diverge away from one another, and a proximate position in which the second end portions are moved toward one another. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension.

In a second embodiment of the present invention, the dental floss holder comprises a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a spaced apart position in which the second end portions of the arms diverge away from one another, and a proximate position in which the second end portions are moved toward one another. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension. Connecting means releasably connects terminal ends of the second end portions of the arms to one another. Hence, the tension within the floss material is maintained. The connecting means located at the terminal ends may have a tooth configurations such to provide a connecting condition where the user may engage one tooth or several teeth of the locking means, hence resulting in varying tensioning of the dental floss as desired.

In a third embodiment of the present invention, the dental floss holder comprises a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a spaced apart position in which the second end portions of the arms diverge away from one another, and a proximate position in which the second end portions are moved toward one another. A living hinge is provided for connecting the middle portions of the arms to one another. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension. A finger gripping surface is further provided on the second end portion of each arm to receive fingers of the user. Each finger gripping surface is located adjacent its respective middle portion of the arm.

In a fourth embodiment of the present invention, the dental floss holder comprises a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a spaced apart position in which the second end portions of the arms diverge away from one another, and a proximate position in which the second end portions are moved toward one another. The second end portions of the arms are integrally formed with one another at respective terminal ends thereof. The terminal ends of the second end portions of the arms define a pointed member for stimulating a gingival area of an oral cavity. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension.

In a fifth embodiment of the present invention, the dental floss holder comprises a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a spaced apart position in which the second end portions of the arms diverge away from one another, and a proximate position in which the second end portions are moved toward one another. The first end portions of the arms project rearwardly from the middle and second end portions. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension. A finger gripping surface is further provided on the second end portion of each arm to receive fingers of the user. The finger gripping surface is located adjacent the middle portion of the arm wherein it projects forwardly with respect to the first and second end portions.

It is, therefore, a purpose of the present invention to provide a dental floss holder in which the tension of dental floss held by the holder can be manipulated to achieve a desired tension for increasing the effectiveness of flossing.

A further purpose of the present invention is to provide a dental floss holder in which the tension of the dental floss can be adjusted and locked at a certain tension.

Another purpose of the present invention is to provide a dental floss holder which is easy to use and manipulate by hand.

Yet another purpose of the present invention is to provide a dental floss holder which can be used to stimulate a gingival area of an oral cavity.

A further purpose of the present invention is to provide a dental floss holder which simple in design and cost-efficient to manufacture.

BRIEF DESCRIPTION OF THE DRAWINGS

The foregoing summary, as well as the following detailed description of a preferred embodiment of the invention, will be better understood when read in conjunction with the appended drawings. For purposes of illustrating the invention, there is shown in the drawings an embodiment which is presently preferred. It should be understood, however, that the invention is not limited to the precise arrangement and instrumentality shown. In the drawings:

FIG. 1A is a rear elevational view of the dental floss holder in which second end portions of arms of the dental floss holder are illustrated in a spaced apart position;

FIG. 1B is an enlarged fragmentary view of the second end portions of the arms of the dental floss holder;

FIG. 7 is a front elevational view of a dental floss holder of a second preferred embodiment;

FIG. 8 is a right side elevational view of the dental floss holder illustrated in FIG. 7;

FIG. 9 is a left side elevational view thereof;

FIG. 10 is a rear elevational view thereof;

FIG. 11 is a top plan view thereof;

FIG. 12 is a bottom plan view thereof;

FIG. 13 is a front elevational view of a dental floss holder of a third preferred embodiment;

FIG. 14 is a right side elevational view of the dental floss holder illustrated in FIG. 13;

FIG. 15 is a left side elevational view thereof;

FIG. 16 is a rear elevational view thereof;

FIG. 17 is a top plan view thereof;

FIG. 18 is a bottom plan view thereof;

FIG. 19 is a front elevational view of a dental floss holder of a fourth preferred embodiment;

FIG. 20 is a right side elevational view of the dental floss holder illustrated in FIG. 19;

FIG. 21 is a left side elevational view thereof;

FIG. 22 is a rear elevational view thereof;

FIG. 23 is a top plan view thereof;

FIG. 24 is a bottom plan view thereof;

FIG. 25 is a front elevational view of a dental floss holder of a fifth preferred embodiment;

FIG. 26 is a right side elevational view of the dental floss holder illustrated in FIG. 25;

FIG. 27 is a left side elevational view thereof;

FIG. 28 is a rear elevational view thereof;

FIG. 29 is a top plan view thereof;

FIG. 30 is a bottom plan view thereof;

FIG. 31 is a front elevational view of a dental floss holder of a sixth preferred embodiment;

FIG. 32 is a right side elevational view of the dental floss holder illustrated in FIG. 31;

FIG. 33 is a left side elevational view thereof;

FIG. 34 is a rear elevational view thereof;

FIG. 35 is a top plan view thereof;

FIG. 36 is a bottom plan view thereof; and

FIG. 37 is a perspective view of a dental floss holder of a seventh preferred embodiment.

DETAILED DESCRIPTION OF THE INVENTION

First Preferred Embodiment

Figure 5:
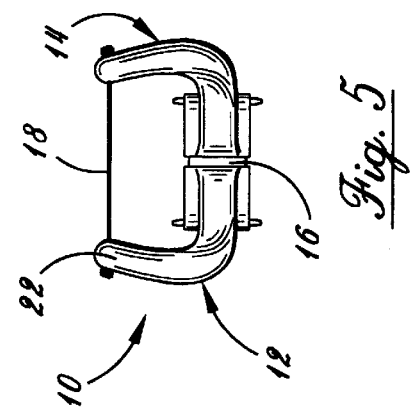
FIG. 5 is a top plan view thereof.
Figure 6:
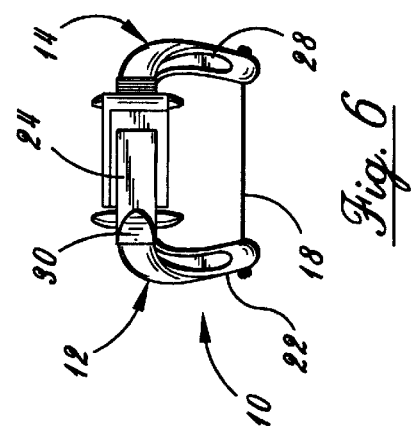
FIG. 6 is a bottom plan view thereof.
Figure 4:
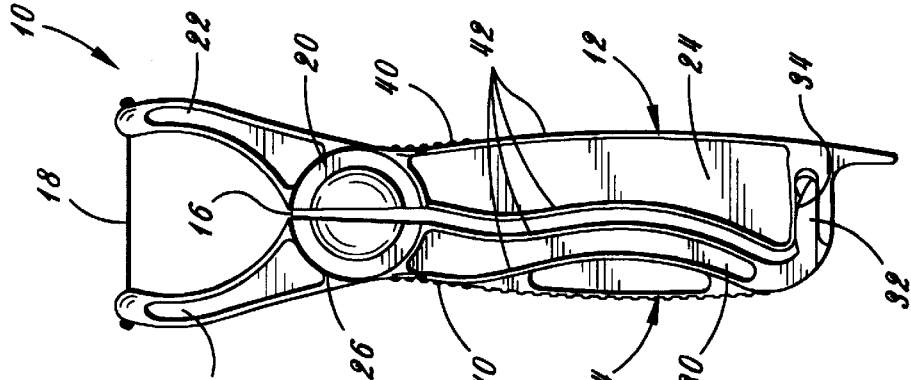
FIG. 4 is a rear elevational view thereof.

Referring now to the drawings, wherein similar reference characters designate corresponding parts throughout the several views, a first preferred embodiment of a dental floss holder the present invention is generally illustrated at 10 in FIGS. 1–6. The dental floss holder 10 includes a pair of arms, generally indicated at 12, 14, which are connected to one another by a living hinge 16.

Preferably, the arms 12, 14 are fabricated from any suitable polymeric material, such as medical grade polypropylene for use in Class 1 FDA medical devices. Dental floss 18 is connected to the arms 12, 14 so that it spans between the two arms in the manner illustrated in the drawings. The arms 12, 14 are constructed in such a way that the tension of the dental floss 18 can be adjusted so as to achieve to the aforementioned flossing method described above. Specifically, the dental floss can be manipulated to have a relatively high tension when positioning the floss between the user's teeth and a relatively low tension when flossing (i.e., wrapping the floss around the user's teeth). The dental floss 18 can also be fabricated from any suitable material, such as nylon or polytetrafluoroethylene ("PTFE"), for example.

As shown, the left-hand arm 12 has a middle portion 20, a first (upper) end portion 22, and a second (lower) end portion 24. Similarly, the right-hand arm 14 has a middle portion 26, a first (upper) end portion 28, and a second (lower) end portion 30. The first end portions 22, 28 of the arms 12, 14 curve outwardly and rearwardly (see FIG. 5) away from their respective middle portions 20, 26. The dental floss 18 is attached to the upper ends of the first end portions 22, 28 of the arms 12, 14 in a manner to be described below. The construction of the first end portions 22, 28 enable the dental floss 18 to project away from the middle portions 20, 26 and the second end portions 24, 30 of the arms 12, 14, respectively, so that the dental floss can be easily positioned between the user's teeth.

Figure 1:
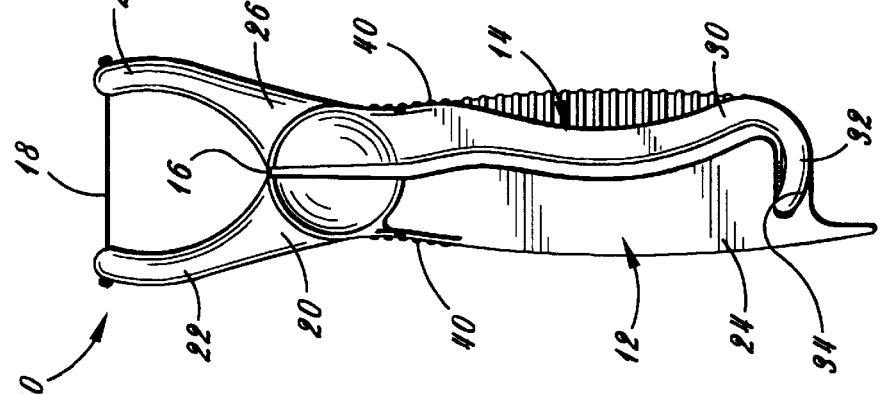
FIG. 1 is a front elevational view of a dental floss holder of a first preferred embodiment of the present invention.
Figure 3:
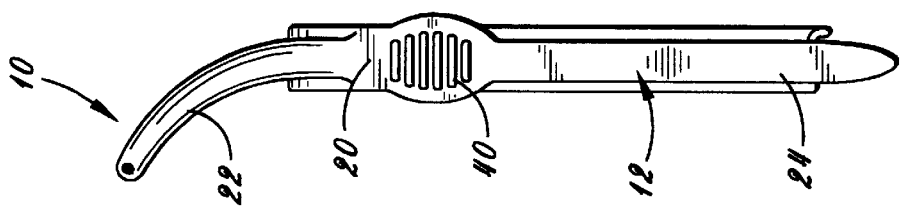
FIG. 3 is a left side elevational view thereof.

Referring specifically to FIGS. 1 and 1A, the second end portions 24, 30 of the arms 12, 14 are movable between a spaced apart position (FIG. 1A) in which the second end portions of the arms diverge away from one another, and a proximate position (FIG. 1) in which the second end portions are moved toward one another. This pivoting action is achieved about the middle portions 20, 26 of the arms 12, 14 which are positioned proximate to one another by the living hinge 16 so as to define a pivot. Preferably, the living hinge 16 is approximately 0.020 inch long, and has a thickness between 0.005 inch and 0.030 inch, to create a "living hinge".

This construction results in the dental floss 18 having a first tension (e.g., relatively slack) when the second end portions 24, 30 of the arms 12, 14 are in their spaced apart position (FIG. 1A) and a second tension (e.g., relatively taut) when the second end portions are in their proximate position. Thus, when using the dental floss holder 10 of the present invention, the user can manipulate the second end portions 24, 30 to their proximate position so that the dental floss 18 is taut for moving the dental floss between the user's teeth. Upon entering the space between the teeth, the user can release the pressure applied on the second end portions 24, 30 so that they move back to their spaced apart position for loosening the tension on the dental floss 18. In this position, the dental floss 18 is sufficiently loose so that it can be wrapped about the user's teeth during flossing.

Turning now to FIG. 1B, the lower ends of the second end portions 24, 30 are provided with means of the present invention for releasably connecting the second end portions of the arms 12, 14 to one another. As shown, the left-hand arm 12 has an inwardly projecting detent 32 formed thereon. The right-hand arm 14 has a recess 34 formed therein for receiving the detent 32 of the left-hand arm 12 therein to releasably connect the second end portions 24, 30 of the arms to one another. The upper edge of the detent has several teeth 36 formed thereon which mate with teeth 38 formed on the second end portion 30 of the right-hand arm 14 within the recess 34. This construction enables the user of the dental floss holder 10 to adjust the lateral position of the arms 12, 14 for increasing the tightness of the dental floss 18. The further the detent 32 projects within the recess 34, the more the tension of the dental floss 18 increases. The teeth 36, 38 also serve the purpose of locking the arms 12, 14 relative to one another, thus enabling the user to cease applying pressure on the second end portions 24, 30 during flossing. It should be noted that any suitable release mechanism for releasing the detent 32 from the recess 34 of the second end portion 30 of the right-hand arm 14 can be provided.

Figure 2:
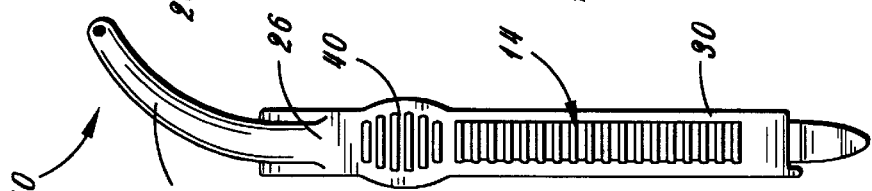
FIG. 2 is a right side elevational view of the dental floss holder illustrated in FIG. 1.

Additionally, the dental floss holder 10 includes finger gripping surfaces 40 provided on the second end portions 24, 30 of the arms 12, 14. As shown, the finger gripping surfaces 40 are located adjacent the middle portions 20, 26 of the arms 12, 14, respectively. Each finger gripping surface 40 is slightly wider than the rest of the arm and includes relatively small protuberances which assist the user in gripping the arms 12, 14 of the dental floss holder 10. As best shown in FIGS. 1 and 2, these protuberances extend along the entire outer edge 42 of arm 14.

Moreover, ribs 40 are formed on the back side of the arms 12, 14 (see FIG. 4) of the dental floss holder 10 for rigidifying the arms during use. Unlike the embodiments that are discussed below, the dental floss holder 10 disclosed in FIGS. 1–6 does not flex a considerable amount, except for the first end portions 22, 28 upon applying a tightening force on the dental floss 18.

As with the other embodiments of the present invention described herein, the dental floss holder 10 is preferably fabricated by a thermal injection molding process. The dental floss 18 is attached to the first end portions 22, 28 of the arms 12, 14 by laying the dental floss within a mold (not shown) used to make the dental floss holder 10. The dental floss 18 preferably has a rectangular cross section and the first end portions 22, 28 of the arms 12, 14 are molded around the dental floss to create a mechanical attachment of the dental floss to the first end portions of the arms. Ends of the dental floss 18 are then cut off in any well known manner so that they cannot back through the openings (not shown) which receive the dental floss.

Second Preferred Embodiment

Turning now to FIGS. 7–12, there is generally indicated at 50 a dental floss holder of a second preferred embodiment. This dental floss holder 50 includes a pair of symmetrically-shaped arms generally indicated at 52, 54. The left-hand arm has a middle portion 56, a first (upper) end portion 58, and a second (lower) end portion 60. Similarly, the right-hand arm also has a middle portion 62, a first (upper) end portion 64, and a second (lower) end portion 66. A living hinge 68 is provided for connecting the middle portions 56, 62 of the arms 52, 54 to one another. As with holder 10, the first end portions 58, 64 of the dental floss holder 50 of this embodiment curve outwardly and rearwardly (see FIG. 11) away from their respective middle portions 56, 62. Dental floss 70 is attached to the upper ends of the first end portions 58, 64 of the arms 52, 54 in the same fashion described above.

The living hinge 68 prevents the over rotation of the first end portions 58, 64 upon moving the second end portions 60, 66 together. Thus, the living hinge 68 substantially precludes the snapping off of the dental floss 70 or one of the arms 52, 54 caused by applying too much pressure on the arm when moving them close together. It should be noted, however, that living hinge 68 may or may not be present in any one element of the present invention.

One major difference between dental floss holder 50 and dental floss holder 10 is that the second end portions 60, 66 of the arms 52, 54 of holder 50 are integrally formed with one another at respective terminal ends thereof. As shown, the terminal ends of the second end portions 60, 66 define a pointed member 72 which can be utilized by the user of the dental floss holder 50 to stimulate a gingival area of the user's oral cavity. In this embodiment, the arms 52, 54 are flexible; thus, the second end portions 60, 66 can be moved toward one another for increasing the tension of the dental floss 70. This results in the first end portions 58, 64 pivoting about the middle portions 56, 62 away from one another for increasing the tension of the dental floss 70.

This construction results in the dental floss 70 having a first tension (e.g., relatively slack) when the second end portions 60, 66 of the arms 52, 54 are in their relaxed condition and a second tension (e.g., relatively taut) when the second end portions are moved toward one another. Thus, when using the dental floss holder 50 of the present embodiment, the user can manipulate the second end portions 60, 66 to their proximate position so that the dental floss 70 is taut for moving the dental floss between the user's teeth. In its relaxed position, the dental floss 70 is less taut for manipulating the dental floss around the user's teeth.

Still referring to FIGS. 6–12, the dental floss holder further includes finger gripping surfaces 74 provided on the second end portions 60, 66 of the arms 52, 54 adjacent the middle portions 56, 62 of the arms. As with the finger gripping surfaces 40 of holder 10, the finger gripping surfaces 74 are slightly wider than the rest of the arms 52, 54 and include relatively small protuberances which assist the user in gripping the arms of the dental floss holder 50.

Third Preferred Embodiment

Turning now to FIGS. 13–18, a dental floss holder 80 of a third preferred embodiment is shown. This dental floss holder 80 is similar to holder 50 of FIGS. 7–12, and in this regard, corresponding parts are designated by similar reference characters throughout the views. The primary difference between holders 50 and 80 is that dental floss holder 80 has a finger gripping surface 82 which is longer in length than finger gripping surface 74 of holder 50. The increased surface area of finger surface 82 enables the user to better grasp the dental floss holder 80 when flossing.

Fourth and Fifth Preferred Embodiments

FIGS. 19–30 illustrate dental floss holders, generally designated at 90, 100, of fourth and fifth preferred embodiments, respectively. Dental floss holders 90, 100 are substantially similar to dental floss holders 50, 80, except that they lack the finger gripping surfaces 74, 72 described above. As shown, dental floss holder 90 is almost identical to holder 100, except holder 90 includes the living hinge 68, whereas holder 100 lacks this feature.

Sixth Preferred Embodiment

Turning to FIGS. 31–36, there is generally indicated at 110 a dental floss holder of a sixth preferred embodiment. As shown, this dental floss holder 110 is substantially identical to holders 50, 80 of FIGS. 7–18, but for the construction of its finger gripping surfaces 112. As shown, the finger gripping surfaces 112 project forwardly with respect to the middle portions 56, 62 and the second end portions 60, 66. This construction improves the motion of the first end portions 58, 64 upon squeezing together the second end portions 60, 66 at the finger gripping surfaces 112 for increasing the tension of the dental floss 70. Specifically, the offset nature of the finger gripping surfaces 112, upon being pressed together by the user, causes the slight forward rotation of the arms 52, 54 for ensuring that the dental floss 70 is tightened rather than loosened. As described above, the living hinge 68 prevents the over pivoting of the first end portions 58, 64 which can result from squeezing the second end portions 60, 66 too tightly together. This can result in the dental floss 70 disengaging the one of the first end portions 58, 64 thereby destroying the dental floss holder 110.

Seventh Preferred Embodiment

Lastly, turning to FIG. 37, a dental floss holder is generally indicated at 120. As shown, dental floss holder 120 comprises a yoke section generally indicated at 122 having a straight member 124 with first and second ends 126, 128, and a pair of outwardly diverging arms 130, 132 connected one another at the first end 126 of the straight member 124. The yoke section 122, at the junction of the straight member 124 and the pair of arms 130,132, has a slot 134 formed therein, the purpose of which will be discussed in greater detail below.

A living hinge 136 is attached to the second end 128 of the straight member 124, the living hinge being constructed similarly to the living hinges described above. A pivoting member 138 is attached to the living hinge 136 and extends away from the straight member 124 of the yoke section 122 in the manner depicted in FIG. 37. The pivoting member 138 has an outwardly projecting wedge element 140, and is hingedly movable about the living hinge 136 between a first position in which the pivoting member 138 is generally parallel to the straight member 124 and a second position in which the wedge element 140 of the pivoting member 138 is moved into engagement with the straight member 124 and received within the slot 134 for moving the pair of arms 130, 132 away from one another. The reception of the wedge element 140 within the slot 134 spreads the arms 130,132 apart.

Dental floss 142 is attached to the ends of the arms 130,132 in the manner described above. The dental floss 142 having a first tension when the pivoting member 138 is in its first position and a second tension when the pivoting member 138 is in its second position. In this arrangement, the first tension of the dental floss 142 is less than the second tension. Thus, it should be noted that with dental floss holder 120, the tension of the dental floss 142 can be increased after initial use thereof by simply pivoting the pivoting member 138 to its second position.

Although a few exemplary embodiments of the present invention have been described in detail above, those skilled in the art readily appreciate that many modifications are possible without materially departing from the novel teachings and advantages which are described herein. Accordingly, all such modifications are intended to be included within the scope of the present invention, as defined by the following claims.

Having described the invention, what is claimed is:

1. A dental floss holder comprising:
    a pair of arms, each arm having a middle portion and first and second opposite end portions, said first end portion of each arm curving outwardly away from its respective middle portion, said middle portions of the arms being positioned proximate one another so as to define a pivot, said second end portions being movable between a first position in which the first end portions of the arms diverge away from one another, and a second position in which the first end portions are moved toward one another, dental floss material having one end secured to the first end portion of one arm and an opposite end secured to the first end portion of the other arm, said dental floss material having a tension that is adjustable between a first tension when the first end portions are in their spaced apart position and a second tension when the first end portions are moved toward one another, in the absence of a locking mechanism, said first tension being greater than said second tension, and said second end portions of the arms having terminal ends defining a pointed member for stimulating a gingival area of an oral cavity.

2. The dental floss holder as set forth in claim 1 further comprising a living hinge connecting the middle portions of said arms to one another at said pivot.

3. The dental floss holder as set forth in claim 2, said living hinge being approximately 0.020 inch long.

4. The dental floss holder as set forth in claims 2 or 3, said living hinge having a thickness between 0.005 inch and 0.030 inch.

5. The dental floss holder as set forth in claims 1 or 2 further comprising, for the second end portion of each arm, a finger gripping surface for receiving fingers of a user.

6. The dental floss holder as set forth in claim 5, said finger gripping surface being located adjacent the middle portion of the arm.

7. The dental floss holder as set forth in claim 1, said first end portions of the arms projecting outwardly from the middle and second end portions.

8. The dental floss holder as set forth in claim 5, said finger gripping surface projecting outwardly with respect to the first and second end portions.

9. The dental floss holder as set forth in claims 1, 2 or 5, said second end portions of the arms being integrally formed with one another at respective terminal ends thereof.

10. A dental floss holder comprising:

a pair of arms, each arm having a middle portion and first and second opposite end portions, said first end portion of each arm curving outwardly away from its respective middle portion, said middle portions of the arms being positioned proximate one another so as to define a pivot, said second end portions being movable between a first position in which the first end portions of the arms diverge away from one another, and a second position in which the first end portions are moved toward one another;

a living hinge connecting the middle portions of said arms to one another;

dental floss material having one end secured to the first end portion of one arm and an opposite end secured to the first end portion of the other arm, said dental floss material having a first tension when the first end portions are in their spaced apart position and a second tension when the first end portions are moved toward one another, said first tension being greater than said second tension; and a finger gripping surface for the second end portion of each arm to receive fingers of the user, each said finger gripping surface being located adjacent the middle portion of the arm;

said second end portions of the arms being integrally formed with one another at respective terminal ends thereof, said terminal ends of the second end portions of the arms defining a pointed member for stimulating a gingival area of an oral cavity.

11. The dental floss holder as set forth in claim 10, said living hinge being approximately 0.020 inch long.

12. The dental floss holder as set forth in claims 10 or 11, said living hinge having a thickness between 0.005 inch and 0.030 inch.

13. The dental floss holder as set forth in claim 10, said first end portions of the arms projecting rearwardly from the middle and second end portions.

14. A dental floss holder comprising:

a pair of arms, each arm having a middle portion and first and second opposite end portions, said first end portion of each arm curving outwardly away from its respective middle portion, said middle portions of the arms being positioned proximate one another so as to define a pivot, said second end portions being movable between a first position in which the first end portions of the arms diverge away from one another, and a second position in which the first end portions are moved toward one another, said second end portions of the arms being integrally formed with one another at respective terminal ends thereof, said terminal ends of the second end portions of the arms defining a pointed member for stimulating a gingival area of an oral cavity; and dental floss material having one end secured to the first end portion of one arm and an opposite end secured to the first end portion of the other arm, said dental floss material having a first tension when the first end portions are in their spaced apart position and a second tension when the first end portions are moved toward one another, said first tension being greater than the first tension.

15. The dental floss holder as set forth in claim 14 further comprising a living hinge connecting the middle portions of said arms to one another.

16. The dental floss holder as set forth in claim 15, said living hinge being approximately 0.020 inch long.

17. The dental floss holder as set forth in claims 15 or 16, said living hinge having a thickness between 0.005 inch and 0.030 inch.

18. The dental floss holder as set forth in claim 14, said first end portions of the arms projecting rearwardly from the middle and second end portions.

19. A dental floss holder comprising:

a pair of arms, each arm having a middle portion and first and second opposite end portions, said first end portion of each arm curving outwardly away from its respective middle portion, said middle portions of the arms being positioned proximate one another so as to define a pivot, said second end portions being movable between a spaced apart position in which the second end portions of the arms diverge away from one another, and a proximate position in which the second end portions are moved toward one another, said first end portions of the arms projecting rearwardly from the middle and second end portions;

dental floss material having one end secured to the first end portion of one arm and an opposite end secured to the first end portion of the other arm, said dental floss material having a tension that is adjustable between a first tension when the second end portions are in their spaced apart position and a second tension when the second end portions are in their proximate position, in the absence of a locking mechanism, said second tension being greater than the first tension;

a finger gripping surface for the second end portion of each arm to receive fingers of the user, said finger gripping surface being located adjacent the middle portion of the arm, said finger gripping surface projecting forwardly with respect to the first and second end portions; and said second end portions of the arms having terminal ends defining a pointed member for stimulating a gingival area of an oral cavity.

20. The dental floss holder as set forth in claim 19 further comprising a living hinge connecting the middle portions of said arms to one another.

21. The dental floss holder as set forth in claim 20, said living hinge being approximately 0.020 inch long.

22. The dental floss holder as set forth in claims 20 or 21, said living hinge having a thickness between 0.005 inch and 0.030 inch.

23. The dental floss holder as set forth in claim 19, said second end portions of the arms being integrally formed with one another at respective terminal ends thereof.

* * * * *